United States Patent
Machida

(10) Patent No.: US 10,660,552 B2
(45) Date of Patent: May 26, 2020

(54) DETECTION DEVICE AND DETECTION METHOD

(71) Applicant: SEIKO EPSON CORPORATION, Tokyo (JP)

(72) Inventor: Yuta Machida, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 243 days.

(21) Appl. No.: 15/666,314

(22) Filed: Aug. 1, 2017

(65) Prior Publication Data

US 2018/0055429 A1 Mar. 1, 2018

(30) Foreign Application Priority Data

Aug. 26, 2016 (JP) ................. 2016-165584

(51) Int. Cl.
| | |
|---|---|
| A61B 5/02 | (2006.01) |
| A61B 5/1455 | (2006.01) |
| A61B 5/021 | (2006.01) |
| A61B 5/026 | (2006.01) |
| A61B 5/0295 | (2006.01) |
| A61B 5/00 | (2006.01) |

(52) U.S. Cl.
CPC .......... *A61B 5/14552* (2013.01); *A61B 5/021* (2013.01); *A61B 5/0261* (2013.01); *A61B 5/0295* (2013.01); *A61B 5/681* (2013.01); *A61B 5/7203* (2013.01); *A61B 2562/0238* (2013.01); *A61B 2562/0242* (2013.01)

(58) Field of Classification Search
CPC ... A61B 5/14552; A61B 5/681; A61B 5/0295; A61B 5/0261; A61B 5/021; A61B 5/7203; A61B 2562/0242; A61B 2562/038
See application file for complete search history.

(56) References Cited

U.S. PATENT DOCUMENTS

| | | | |
|---|---|---|---|
| 5,291,884 A | 3/1994 | Heinemann et al. | |
| 6,181,959 B1 | 1/2001 | Schollermann et al. | |
| 2006/0253007 A1* | 11/2006 | Cheng | A61B 5/0048 600/310 |

FOREIGN PATENT DOCUMENTS

| | | |
|---|---|---|
| JP | H06-505170 A | 6/1994 |
| JP | 2000-507465 A | 6/2000 |
| JP | 2000-325330 A | 11/2000 |
| WO | 92/13482 A1 | 8/1992 |
| WO | 97/36538 A1 | 10/1997 |

* cited by examiner

*Primary Examiner* — Christian Jang
(74) *Attorney, Agent, or Firm* — Oliff PLC

(57) ABSTRACT

A detection device generating first and second detection signals includes: a light-emitting unit that emits light to a measurement part for each of first and second periods repeated on a time axis; a signal generation unit that generates the first detection signal according to a light reception level of the light emitted from the light-emitting unit for each first period and passing along a first path inside the measurement part and the second detection signal according to a light reception level of the light emitted from the light-emitting unit for each second period and passing along a second path different from the first path inside the measurement part; and a control unit that controls a duration of at least one of the first and second periods so that component values of steady components included in the first and second detection signals are closer to each other.

7 Claims, 11 Drawing Sheets

DETECTION DEVICE AND DETECTION METHOD

BACKGROUND

1. Technical Field

The present invention relates to a technology for measuring biological information.

2. Related Art

Various measurement technologies for measuring biological information noninvasively by radiating light to organisms have been proposed in the related art. For example, JP-T-2000-507465 discloses a configuration in which an oxygen saturation amount in an artery is measured from a signal generated by two photodiodes receiving light emitted from an LED and passing through the inside of a finger.

Tissues through which light emitted from an LED passes inside an organism differ depending on conditions of light emission. For example, in the technology of JP-T-2000-507465, a sensor including an LED and two photodiodes is fixed with a finger interposed therebetween. Therefore, the thickness of each tissue inside the fingers varies according to a force applied to the fingers. Accordingly, there is a possibility that the kinds of tissues through which light arriving at the photodiodes passes inside the fingers are different. When the kinds of tissues through which the light arriving at the photodiodes passes inside an organism are different, an error occurs in oxygen saturation amounts calculated from signals generated from the photodiodes.

SUMMARY

An advantage of some aspects of the invention is to provide a technology for measuring detection signals generated to compensate a difference in the kinds of tissues in which a plurality of different paths are located inside a measurement part and further measuring biological information with high precision.

A detection device according to a preferred aspect of the invention, is a detection device generating first and second detection signals used to specify biological information. The detection device includes: a light-emitting unit that emits light to a measurement part for each of first and second periods repeated on a time axis; a signal generation unit that generates the first detection signal according to a light reception level of the light emitted from the light-emitting unit for each first period and passing along a first path inside the measurement part and the second detection signal according to a light reception level of the light emitted from the light-emitting unit for each second period and passing along a second path different from the first path inside the measurement part; and a control unit that controls a duration of at least one of the first and second periods so that component values of steady components included in the first and second detection signals are closer to each other. According to the foregoing configuration, the duration of at least one of the first and second periods mutually repeated on the time axis is controlled such that the component values of the steady components included in the first and second detection signals are closer to each other. Accordingly, compared to a configuration in which the component values of the steady components included in the first and second detection signals are not closer to each other, it is possible to generate the first and second detection signals for compensating a difference in kinds of tissues in which the first and second paths are located inside the measurement part. Further, it is possible to measure biological information with high precision.

In the preferred aspect of the invention, the first and second periods may be alternately repeated at a predetermined cycle. According to the foregoing configuration, the first and second periods are repeated at the predetermined cycle. Accordingly, it is easy to perform a process (A/D conversion) of generating a detection value (digital data) according to a light reception level for each first period and a detection value according to a light reception level for each second period. Since the first and second periods are alternately repeated, sampling the detection value according to the light reception level for each first period and the detection value according to the light reception level for each second period is simplified.

In the preferred aspect of the invention, the light may be coherent light. According to the foregoing configuration, the coherent light is emitted to the measurement part. For example, since the light emission intensity for the first and second periods is controlled, it may be necessary to excessively raise the light emission intensity in the configuration in which the component values of the steady components included in the first and second detection signals are closer to each other. However, when the coherent light is emitted with an excessively strong intensity, a problem of safety such as erroneous emission to the body of a user may occur. By controlling the duration of at least one of the first and second periods, it is not necessary to emit the light with an excessively strong light emission intensity in the configuration in which the component values of the steady components included in the first and second detection signals are closer to each other. Therefore, even when the coherent light is used, the problem of safety is reduced. That is, it is particularly effective when the coherent light is emitted.

In the preferred aspect of the invention, the light-emitting unit may include a first light-emitting element that emits the light passing along the first path for the first period and a second light-emitting element that emits the light passing along the second path for the second period. According to the foregoing configuration, the first light-emitting element emits the light for the first period and the second light-emitting element emits the light for the second period. Accordingly, it is possible to realize the configuration in which the light with different wavelength bandwidth are emitted for the first and second periods more easily than in the configuration in which the light is emitted from the same light-emitting element for the first and second periods.

In the preferred aspect of the invention, the signal generation unit may include a first light-receiving element that receives the light passing along the first path and a second light-receiving element that receives the light passing along the second path and may generate the first detection signal according to a light reception level of the first light-receiving element and the second detection signal according to a light reception level of the second light-receiving element. According to the foregoing configuration, the first detection signal according to the light reception level of the first light-receiving element and the second detection signal according to the light reception level of the second light-receiving element are generated. Accordingly, compared to a configuration in which only one light-receiving element is included, it is possible to individually optimize light reception characteristics (light reception sensitivity in a specific bandwidth), that is, wavelength ranges of the first light-receiving element and the second light-receiving element.

In the preferred aspect of the invention, a light emission intensity of the light emitted for each first period by the light-emitting unit and passing along the first path may be constant and a light emission intensity of the light emitted for each second period by the light-emitting unit and passing along the second path may be constant. According to the foregoing configuration, the light emission intensity of the light emitted for each first period is constant and the light emission intensity of the light emitted for each second period is constant. Accordingly, by controlling the light emission intensity for each first period and each second period, intensity control is not necessary compared to the configuration in which the component values of the steady components included in the first and second detection signals are closer to each other.

A detection method according to a preferred aspect of the invention is a detection method of generating first and second detection signals used to specify biological information. The method may cause a computer to perform: emitting light to a measurement part for each of first and second periods repeated on a time axis; generating the first detection signal according to a light reception level of the light emitted for each first period and passing along a first path inside the measurement part and the second detection signal according to a light reception level of the light emitted for each second period and passing along a second path different from the first path inside the measurement part; and controlling a duration of at least one of the first and second periods so that component values of steady components included in the first and second detection signals are closer to each other. In the foregoing method, the duration of at least one of the first and second periods mutually repeated on the time axis is controlled such that the component values of the steady components included in the first and second detection signals are closer to each other. Accordingly, compared to a configuration in which the component values of the steady components included in the first and second detection signals are not closer to each other, it is possible to generate the first and second detection signals for compensating a difference in kinds of tissues in which the first and second paths are located inside the measurement part. Further, it is possible to measure biological information with high precision.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Figure 1:
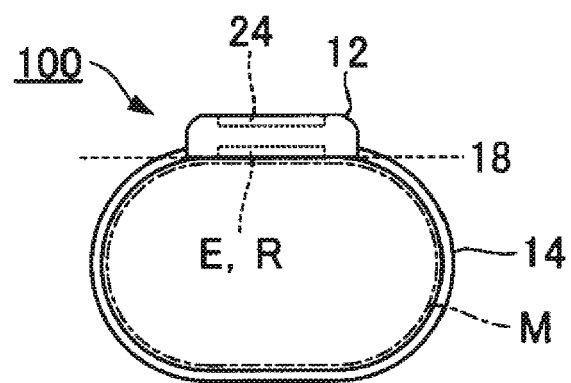
FIG. 1 is a side view illustrating a measurement device according to a first embodiment of the invention.

FIG. 1 is a side view illustrating a measurement device 100 according to a first embodiment of the invention. The measurement device 100 according to the first embodiment is a bioinstrument that measures biological information of a test subject noninvasively and is mounted on a part (hereinafter referred to as a "measurement part") M which is a measurement target of the body of the test subject. The measurement device 100 according to the first embodiment is a wristwatch type portable device that includes a casing 12 and a belt 14 and can be mounted around a wrist of the test subject by winding the belt 14 around the wrist which is an example of a measurement part M. In the first embodiment, oxygen saturation (SpO2) is exemplified as biological information. The oxygen saturation means a ratio (%) of hemoglobin combined with oxygen in hemoglobin in a blood of the test subject and is an index for evaluating a respiratory function of the test subject.

Figure 2:
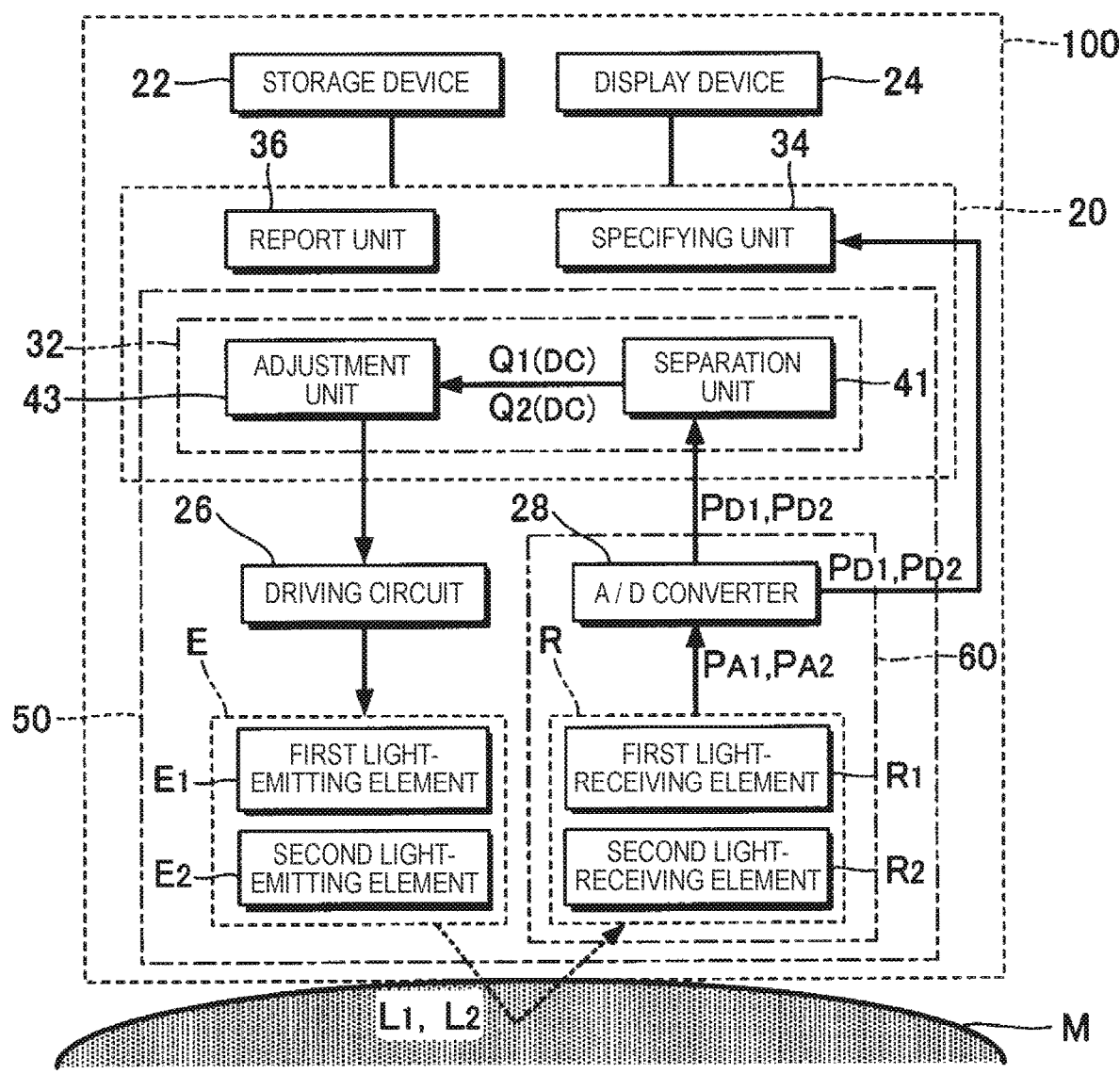
FIG. 2 is a diagram illustrating a functional configuration of the measurement device.

FIG. 2 is a diagram illustrating a functional configuration of the measurement device 100. As exemplified in FIG. 2, the measurement device 100 according to the first embodiment includes a control device 20, a storage device 22, a display device 24, a driving circuit 26, a light-emitting unit E, an A/D converter 28, and a light-receiving unit R. The control device 20 and the storage device 22 are installed inside the casing 12.

The control device 20 is an arithmetic processing device such as a central processing unit (CPU) or a field-programmable gate array (FPGA) and controls the entire measurement device 100. The storage device 22 is configured of, for example, a nonvolatile semiconductor memory and stores a program which is executed by the control device 20 and various kinds of data (for example, a table for specifying oxygen saturation) which are used by the control device 20. The control device 20 according to the first embodiment executes the program stored in the storage device 22 to realize a plurality of functions (a control unit 32, a specifying unit 34, and a report unit 36) measuring oxygen saturation of a test subject. A configuration in which functions of the control device 20 are distributed to a plurality of integrated circuits or a configuration in which some or all of the functions of the control device 20 are realized by dedicated electronic circuits can also be adopted. In FIG. 2, the control device 20 and the storage device 22 are illustrated as separate elements. However, the control device 20 including the storage device 22 can also be realized by, for example, an application specific integrated circuit (ASIC). The display device 24 (for example, a liquid crystal display panel) is installed on the surface (for example, an opposite surface to the measurement part M) of the casing 12, as exemplified in FIG. 1 and displays various images including measurement results under the control of the control device 20. The driving circuit 26 drives the light-emitting unit E.

The light-emitting unit E and the light-receiving unit R in FIG. 2 are sensor modules that generate light reception signals PA (a first light reception signal PA1 and a second light reception signal PA2) according to a state of the measurement part M. The light-emitting unit E and the light-receiving unit R are installed on, for example, an opposite surface (hereinafter referred to as a "detection surface") 18 of the casing 12 to the measurement part M. The detection surface 18 in FIG. 1 is a planar surface or a curve surface. The light-emitting unit E and the light-receiving unit R are installed on the detection surface 18 and are located on one side when viewed from the measurement part M.

The light-emitting unit E in FIG. 2 emits light to the measurement part M. Light L emitted by the light-emitting unit E in the first embodiment is coherent light (that is, laser light) with high coherence. The light-emitting unit E according to the first embodiment includes a first light-emitting element E1 that emits light L1 for a first period T1 and a second light-emitting element E2 that emits light L2 for a second period T2. For example, a vertical cavity surface emitting LASER (VCSEL) emitting the light L from the detection surface 18 to the measurement part M in the vertical direction is appropriately used as each of the first light-emitting element E1 and the second light-emitting element E2. In the first embodiment, the light L1 and the light L2 are different in wavelength $\lambda$. For example, the light L1 is near infrared light (with wavelength $\lambda 1$=800 nm to 1300 nm) and the light L2 is red light (with wavelength $\lambda 2$=600 nm to 800 nm). The first light-emitting element E1 and the second light-emitting element E2 are driven by a driving current supplied from the driving circuit 26 in FIG. 2 to emit the light L.

Figure 3:
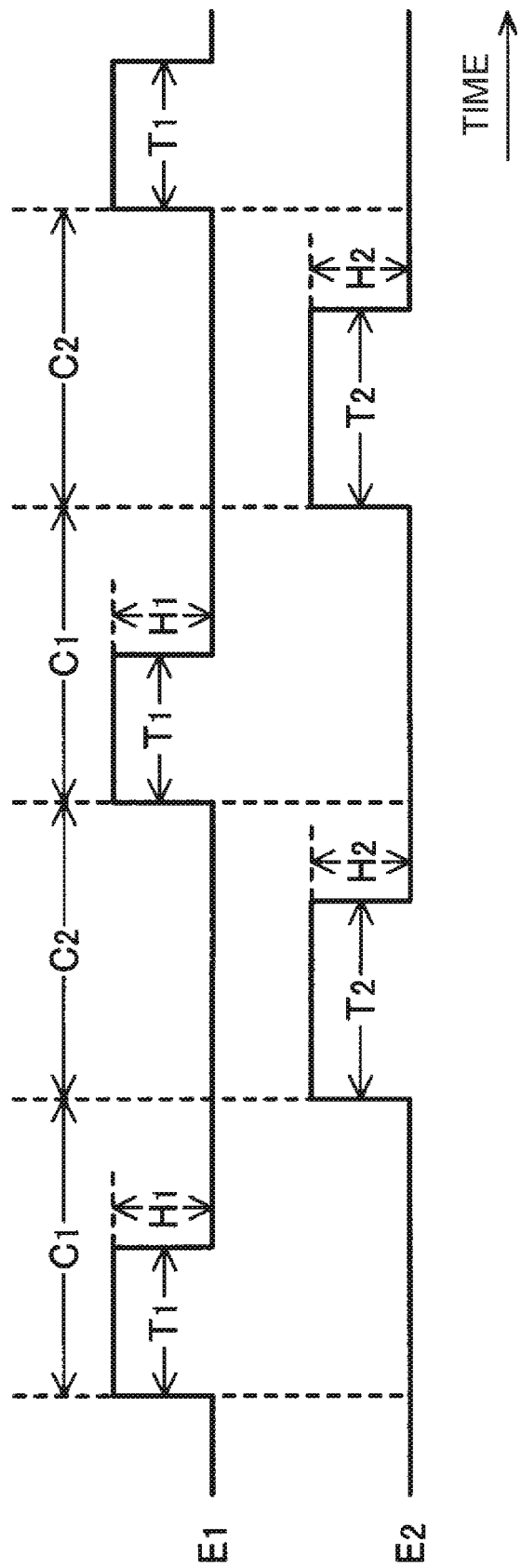
FIG. 3 is a diagram illustrating a light emitting operation by a light-emitting unit.

FIG. 3 is a diagram illustrating a light emitting operation by the light-emitting unit E. The light-emitting unit E emits the light L for each of the first period T1 and the second period T2 repeated on a time axis. As exemplified in FIG. 3, the first period T1 and the second period T2 are alternately repeated at a predetermined cycle C. The cycle C is a cycle sufficiently shorter than a pulse. Each of the first period T1 and the second period T2 is a duration of a part of the cycle C. As exemplified in FIG. 3, a cycle C1 including the first period T1 and a cycle C2 including the second period T2 are alternately repeated on the time axis. The first light-emitting element E1 emits the light L1 with a light emission intensity H1 within the first period T1 of the cycle C1 and is turned off for the cycle C2 and a period other than the first period T1 of the cycle C1. The light emission intensity H1 is constant for each first period T1. The second light-emitting element E2 emits the light L2 with a light emission intensity H2 for a duration equivalent to the second period T2 of the cycle C2 and is turned off at the cycle C1 and a period other than the second period T2 of the cycle C2. The light emission intensity H2 is constant for each second period T2. The light emission intensity H1 and the light emission intensity H2 may be different. The driving circuit 26 supplies a driving current to the first light-emitting element E1 for the first period T1 in response to an instruction from the control device 20 and supplies a driving current to the second light-emitting element E2 for the second period T2. Accordingly, the first light-emitting element E1 emits the light L1 for each first period T1 and the second light-emitting element E2 emits the light L2 for each second period T2.

The light L emitted from the light-emitting unit E (the first light-emitting element E1 and the second light-emitting element E2) is incident on the measurement part M, is repeatedly reflected and scattered inside the measurement part M, is emitted to the side of the detection surface 18, and arrives at the signal generation unit 60 (the light-receiving unit R). That is, the light-emitting unit E and the light-receiving unit R function as reflective optical sensors.

The light-receiving unit R in FIG. 2 generates the first analog light reception signal PA1 and the second analog light reception signal PA2 according to a light reception level of the light arriving from the measurement part M. The light-receiving unit R according to the first embodiment includes a first light-receiving element R1 and a second light-receiving element R2. The first light-receiving element R1 receives the light L1 emitted from the first light-emitting element E1 for each first period T1 and passing inside the measurement part M along a first path B1 and generates the first light reception signal PA1 according to the light reception level. The second light-receiving element R2 receives the light L2 emitted from the second light-emitting element E2 for each second period T2 and passing inside the measurement part M along a second path B2 different from the first path B1 and generates the second light reception signal PA2 according to the light reception level. For example, light conversion elements such as photodiodes (PDs) receiving the light L on the light reception surface opposite to the measurement part M are appropriately used as the first light-receiving element R1 and the second light-receiving element R2.

Figure 4:
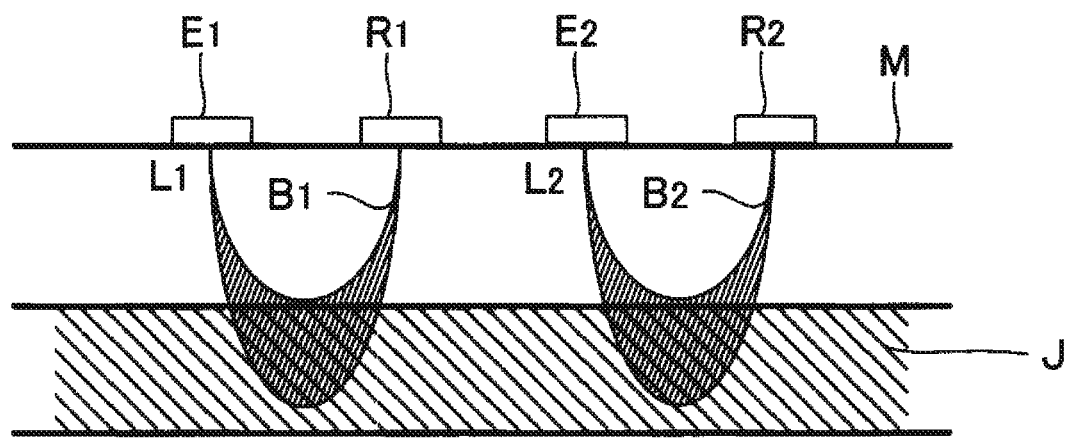
FIG. 4 is a diagram illustrating first and second paths.

FIG. 4 is a diagram illustrating the first path B1 and the second path B2. Each of the first path B1 and the second path B2 refers to, for example, a range in which light arriving from the light-emitting unit E to the light-receiving unit R propagates inside the measurement part M. The first path B1 and the second path B2 mean a range (so-called banana shape) in which light with an intensity exceeding a predetermined value distributes. In the first embodiment, as exemplified in FIG. 4, the first path B1 in which the light L1 arriving from the first light-emitting element E1 to the first light-receiving element R1 and the second path B2 in which the light L2 arriving from the second light-emitting element E2 passes to the second light-receiving element R2 are exemplified. There are a plurality of types of tissues (for example, a blood vessel J) in the measurement part M.

In the first embodiment, as exemplified in FIG. 4, the first light-emitting element E1, the second light-emitting element E2, the first light-receiving element R1, and the second light-receiving element R2 are installed on the detection surface 18 and are located on a straight line. A distance (for example, an center-to-center distance) between the first light-emitting element E1 and the first light-receiving element R1 is equal to a distance between the second light-emitting element E2 and the second light-receiving element R2. As described above, a pair of the first light-emitting element E1 and the first light-receiving element R1 and a pair of the second light-emitting element E2 and the second light-receiving element R2 are installed at different positions on the detection surface 18 in the measurement part M. Therefore, the first path B1 and the second path B2 are different.

Figure 5:
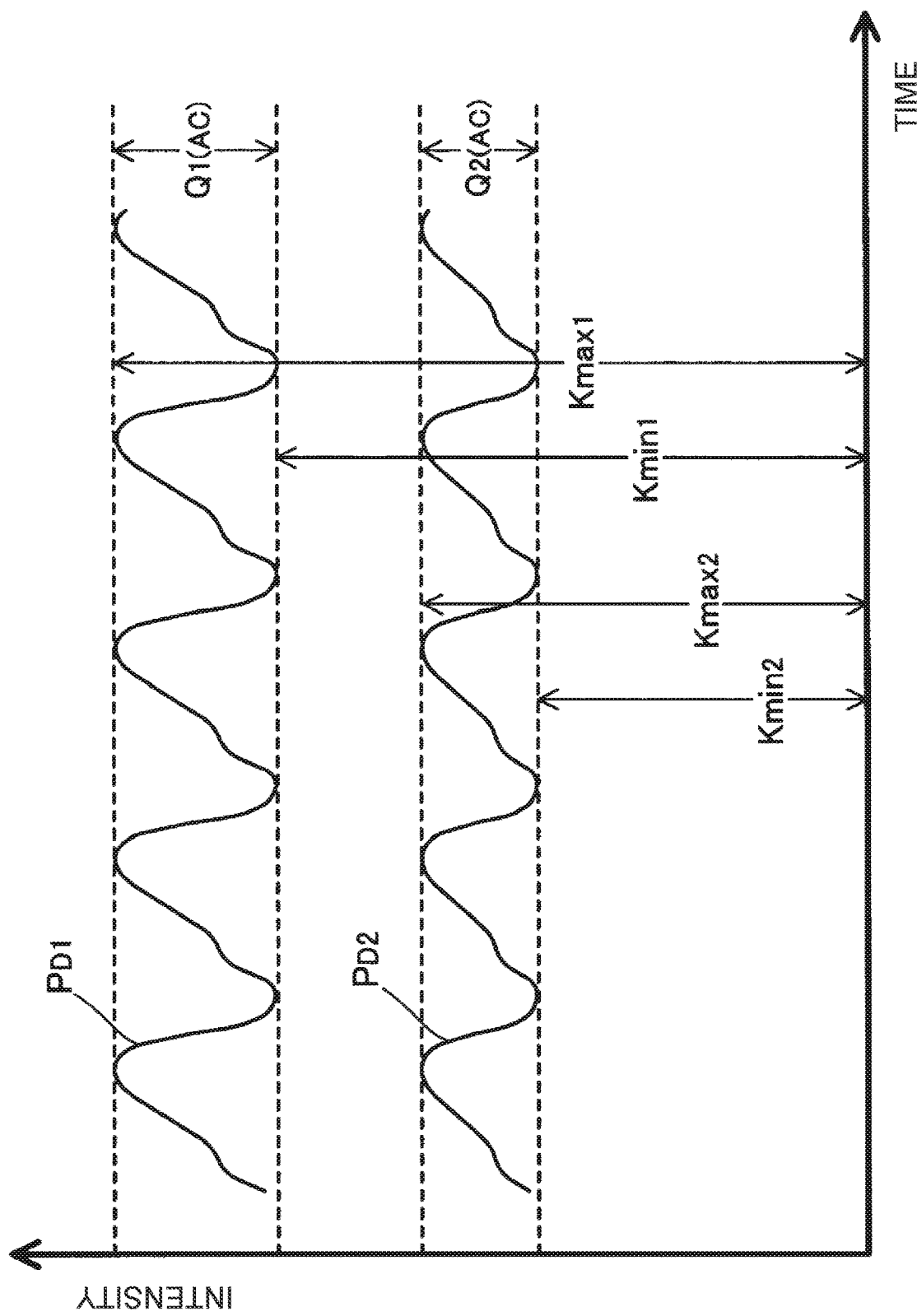
FIG. 5 is a diagram illustrating first and second detection signals.

The A/D converter 28 in FIG. 2 generates a first detection signal PD1 and a second detection signal PD2 used to specify oxygen saturation by performing A/D conversion on the light reception signals PA (analog signals) generated by the light-receiving unit R. Specifically, the A/D converter 28 generates a time series of detection values obtained by performing time integration on the first light reception signal PA1 within the cycle C1 including the first period T1 as the first detection signal PD1 in FIG. 5 and generates a time series of detection values obtained by performing time integration on the second light reception signal PA2 within the cycle C2 including the second period T2 as the second detection signal PD2 in FIG. 5. As described above, since the first period T1 and the second period T2 are repeated at the predetermined cycle C, it is easy to perform a process (that is, A/D conversion) of generating a detection value according to a light reception level for each first period T1 and a detection value according to a light reception level for each second period T2. Since the first period T1 and the second period T2 are alternately repeated, sampling the detection value according to the light reception level for each first period T1 and the detection value according to the light reception level for each second period T2 is simplified.

As understood from the foregoing description, the light-receiving unit R and the A/D converter 28 function as a signal generation unit 60 that generates the first detection signal PD1 according to the light reception level of the light L1 emitted from the light-emitting unit E for each first period T1 and passing along the first path B1 inside the measurement part M and the second detection signal PD2 according to the light reception level of the light L2 emitted from the light-emitting unit E for each second period T2 different from the first path B1 and passing along the second path B2 inside the measurement part M. The signal generation unit 60 includes an amplification circuit that amplifies the light reception signal PA. In FIG. 1, the amplification circuit is not illustrated.

The blood vessel J of the measurement part M is repeatedly expanded and contracted at the same cycle as a heart rate. Since blood flow volumes of blood inside the blood vessel J are different at the time of expansion and contraction, the first detection signal PD1 and the second detection signal PD2 generated by the light-receiving unit R according to the light reception levels from the measurement part M are blood flow signals including periodic variation components corresponding to a variation in the blood flow volume of an artery of the measurement part M, as exemplified in FIG. 5. The first detection signal PD1 and the second detection signal PD2 each include a variation component and a steady component. The variation component is a pulse wave that periodically varies in conjunction with pulsation of the test subject and is extracted, for example, as a high-frequency component of the detection signals PD (PD1 and PD2) by a high-pass filter. On the other hand, the steady component is a component (ideally, a direct-current component maintained steadily) that varies for a sufficiently long time (for example, from several minutes and several hours) compared to the variation component and is extracted, for example, as a low-frequency component of the detection signals PD by a low-pass filter.

Incidentally, when the kinds of tissues in which the light L arriving at the first light-receiving element R1 and the second light-receiving element R2 passes inside an organism are different, that is, when the kinds of tissues in which the first path B1 and the second path B2 in FIG. 4 are located inside the measurement part are different, there is a problem that an error occurs in oxygen saturation specified from the first detection signal PD1 and the second detection signal PD2. Here, component values of the steady components vary according to a kind of tissue in which the paths B1 and B2 of the detection signals PD are located inside the measurement part. That is, when a component value Q1 (DC) of the steady component of the first detection signal PD1 and a component value Q2 (DC) of the steady component of the second detection signal PD2 are the same as each other, there is a high possibility that the kinds of tissues in which the first path B1 and the second path B2 pass are approximate or identical to each other. Accordingly, according to the first embodiment, by controlling a duration of at least one of the first period T1 and the second period T2 so that the component value Q1 (DC) and the component value Q2 (DC) are closer to each other, the first detection signal PD1 and the second detection signal PD2 for compensating a difference in the kinds of tissues in which the first path B1 and the second path B2 are located inside the measurement part M are generated.

The control unit 32 in FIG. 2 includes a separation unit 41 and an adjustment unit 43 and controls a duration of at least one of the first period T1 and the second period T2 so that the component value Q1 (DC) of the steady component of the first detection signal PD1 and the component value Q2 (DC) of the steady component of the second detection signal PD2 are closer to each other. The separation unit 41 calculates the component value Q1 (DC) of the steady component from the first detection signal PD1 and calculates the component value Q2 (DC) of the steady component from the second detection signal PD2. For example, the separation unit 41 calculates an average value ((Kmax1+Kmin1)/2) of a maximum value Kmax1 and a minimum value Kmin1 of an amplitude of the first detection signal PD1 in FIG. 5 as the component value Q1 (DC) and calculates an average value ((Kmax2+Kmin2)/2) of a maximum value Kmax2 and a minimum value Kmin2 of an amplitude of the second detection signal PD2 in FIG. 5 as the component value Q2 (DC). The maximum values Kmax1 and Kmax2 are an average of maximum values for a plurality of cycles and the minimum values Kmin1 and Kmin2 are averages of minimum values for the plurality of cycles. A light reception level at the time of turning off the light-receiving unit R can also be subtracted from the detection signal PD (that is, at the time of receiving only ambient light such as solar light or illumination light) and the steady component can be calculated.

The adjustment unit 43 in FIG. 2 controls the duration of at least one of the first period T1 and the second period T2 so that the component value Q1 (DC) and component value Q2 (DC) calculated by the separation unit 41 are closer to each other. Specifically, the adjustment unit 43 performs a process of adjusting the durations of the first period T1 and the second period T2 according to a result obtained by comparing a predetermined threshold with an index indicating a difference between the component value Q1 (DC) and the component value Q2 (DC) (for example, an absolute value |Q1 (DC)–Q2 (DC)| of the difference between the component value Q1 (DC) and the component value Q2 (DC)). For example, when the index exceeds the predetermined threshold, the adjustment unit 43 adjusts the duration (duty ratio) of at least one of the first period T1 and the second period T2 while the duration of each cycle C is constant, so that the component value Q1 (DC) and the component value Q2 (DC) are closer to each other (ideally, identical). The predetermined threshold is selected experimentally or statistically.

When the duration of the first period T1 is set to be long, the component value Q1 (DC) tends to increase. Similarly, when the duration of the second period T2 is set to be long, the component value Q2 (DC) tends to increase. Accordingly, when the component value Q1 (DC) is greater than the component value Q2 (DC), the adjustment unit 43 performs at least one of shortening of the first period T1 and lengthening of the second period T2 to approach the component value Q1 (DC) and the component value Q2 (DC) each other. Conversely, when the component value Q1 (DC) is less than the component value Q2 (DC), the adjustment unit 43 performs at least one of lengthening of the first period T1 and shortening of the second period T2 to approach the component value Q1 (DC) and the component value Q2 (DC) each other. Specifically, the adjustment unit 43 controls the durations of the first period T1 and the second period T2 by giving an instruction of a duration in which a driving current is supplied to the light-emitting unit E to the driving circuit 26. The driving circuit 26 in FIG. 2 supplies the driving current to the light-emitting unit E for the first period T1 and the second period T2 of the duration according to an instruction from the control unit 32 (the adjustment unit 43). As understood from the foregoing description, the light-emitting unit E, the signal generation unit 60, and the control unit 32 function as a detection device 50 that generates the first detection signal PD1 and the second detection signal PD2 used to specify biological information. That is, the detection device 50 is provided in a form of a sensor module including the light-emitting unit E, the signal generation unit 60, and the control unit 32 and can be mounted on the measurement device 100.

The specifying unit 34 specifies oxygen saturation of the test subject from the first detection signal PD1 and the second detection signal PD2 generated by the signal generation unit 60. The oxygen saturation can be specified by the specifying unit 34 by adopting any known technology. For example, the oxygen saturation can be specified using correspondence between a variation ratio Φ calculated from the first detection signal PD1 and the second detection signal PD2 and the oxygen saturation.

Here, when the oxygen saturation is specified without approaching the component value Q1 (DC) and the component value Q2 (DC) to each other, the variation ratio Φ is a ratio of a component ratio X2 to a component ratio X1, as expressed in Formula (1) below. The component ratio X1 is an intensity ratio of a variation width Q1 (AC) of the variation component included in the first detection signal PD1 to the component value Q1 (DC) of the steady component. The component ratio X2 is an intensity ratio of a variation width Q2 (AC) of the variation component included in the second detection signal PD2 to the component value Q2 (DC) of the steady component. The variation width Q (AC) of the variation component is the amplitude of the detection signal PD, as exemplified in FIG. 5. The variation width Q (AC) of the variation component can be calculated by adopting any know technology. For example, the specifying unit 34 calculates a difference (Kmax1−Kmin1) between the maximum value Kmax1 and the minimum value Kmin1 of the first detection signal PD1 in FIG. 5 as the variation width Q1 (AC) of the first detection signal PD1 and calculates a difference (Kmax2−Kmin2) between the maximum value Kmax2 and the minimum value Kmin2 of the second detection signal PD2 in FIG. 5 as the variation width Q2 (AC) of the second detection signal PD2. The variation ratio Φ in Formula (1) and oxygen saturation are correlated.

$$\Phi = \frac{X_2}{X_1} = \frac{Q_{2(AC)}/Q_{2(DC)}}{Q_{1(AC)}/Q_{1(DC)}} \quad (1)$$

Here, as described above, in the first embodiment, the component value Q1 (DC) and the component value Q2 (DC) are closer to each other by causing the control unit 32 to control the durations of the first period T1 and the second period T2. That is, the ratio (Q1 (DC)/Q2 (DC)) of the component value Q1 (DC) to the component value Q2 (DC) is a value close to 1. Accordingly, when the ratio (Q1 (DC)/Q2 (DC)) is assumed to be 1, the component value Q1 (DC) in the denominator of Formula (1) and the component value Q2 (DC) in the numerator are erased. Therefore, Formula (1) is simplified to Formula (2) below.

$$\Phi = \frac{Q_{2(AC)}}{Q_{1(AC)}} \quad (2)$$

The specifying unit 34 extracts the variation width Q1 (AC) of the first detection signal PD1 and the variation width Q2 (AC) of the second detection signal PD2 by analyzing the first detection signal PD1 and the second detection signal PD2 and calculates the variation ratio Φ from Formula (2). Then, the specifying unit 34 specifies oxygen saturation corresponding to the variation ratio Φ calculated from the first detection signal PD1 and the second detection signal PD2 as a measurement result with reference to a table in which each numerical value of the variation ratio Φ matches each numerical value of the oxygen saturation.

As understood from the foregoing description, since the durations of the first period T1 and the second period T2 are controlled such that the component value Q1 (DC) and the component value Q2 (DC) are closer to each other, the variation ratio Φ can be calculated by Formula (2). Accordingly, the process of calculating the variation ratio Φ is further simplified than in a configuration in which oxygen saturation is specified without approaching the component value Q1 (DC) and the component value Q2 (DC) to each other (that is, a configuration in which the variation ratio Φ is calculated by Formula (1)). Further, the process of specifying the oxygen saturation is simplified.

The report unit 36 causes the display device 24 to display the oxygen saturation specified by the specifying unit 34. A configuration also is suitable in which when the oxygen saturation is varied to a numerical value out of a predetermined range, the report unit 36 reports a warning (a possibility of a disorder of a respiratory function) to a user.

Figure 6:
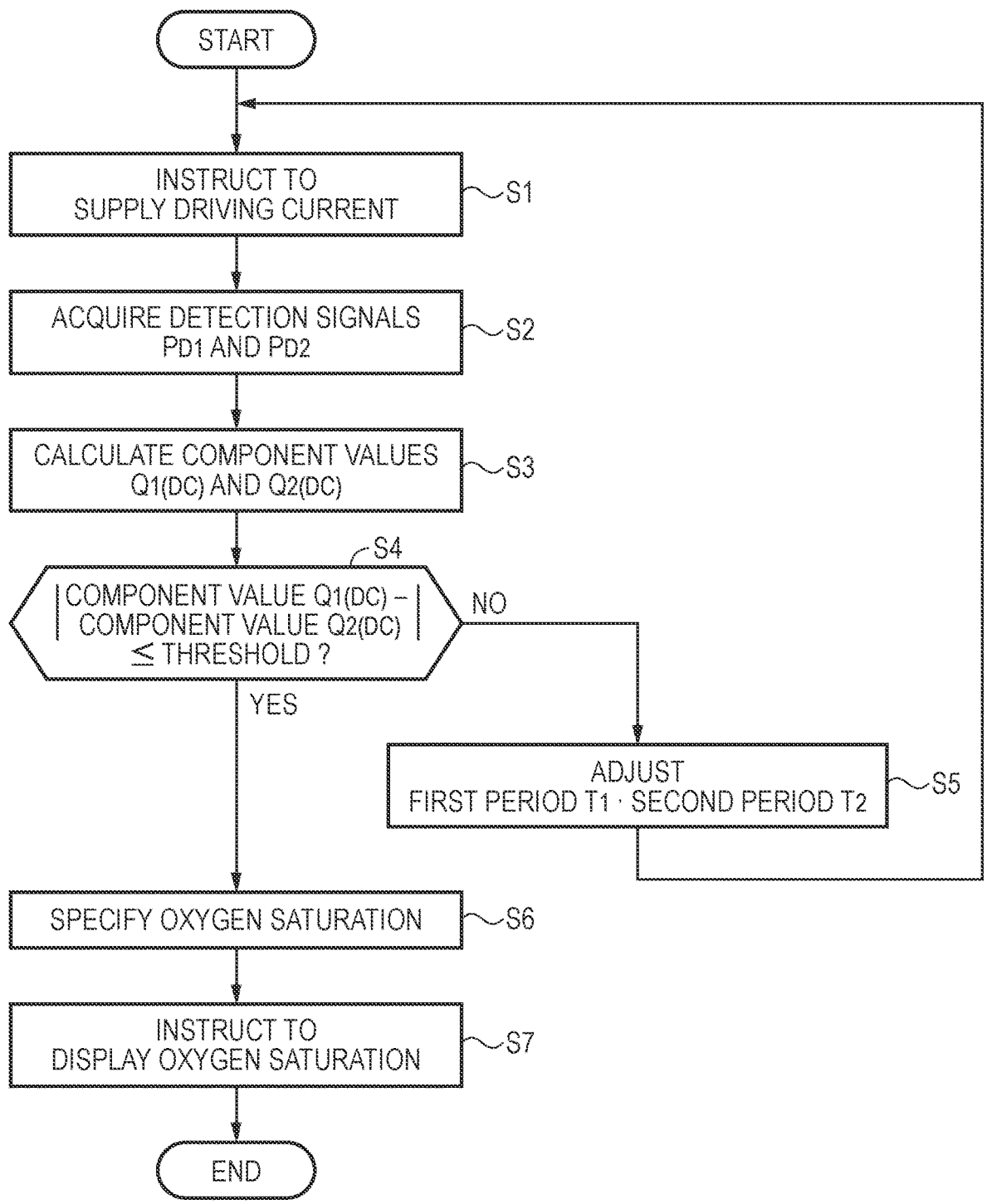
FIG. 6 is a flowchart illustrating a process of a control device.

FIG. 6 is a flowchart illustrating a process of the control device 20. The process of FIG. 6 is started using an instruction to activate the measurement device 100 from the user as a trigger. The adjustment unit 43 instructs the driving circuit 26 to supply a driving current for the first period T1 and the second period T2 of the durations set to predetermined initial values (S1). The driving current supplied from the driving circuit 26 enables the first light-emitting element E1 to emit the light L1 to the measurement part M for each first period T1 and enables the second light-emitting element E2 to emit the light L2 to the measurement part M for each second period T2. The signal generation unit 60 generates the first detection signal PD1 according to the light reception level of the light L1 emitted from the first light-emitting element E1 for each first period T1 and passing along the first path B1 and the second detection signal PD2 according to the light reception level of the light L2 emitted from the second light-emitting element E2 for each second period T2 and passing along the second path B2. The separation unit 41 acquires the first detection signal PD1 and the second detection signal PD2 generated by the signal generation unit 60 (S2). The separation unit 41 calculates the component value Q1 (DC) of the acquired first detection signal PD1 and the component value Q2 (DC) of the acquired second detection signal PD2 (S3).

The adjustment unit 43 determines whether the absolute value |Q1 (DC)−Q2 (DC)| of the difference between the calculated component value Q1 (DC) and component value Q2 (DC) is less than the predetermined threshold (S4). When the absolute value |Q1 (DC)−Q2 (DC)| is greater than the predetermined threshold (NO in S4), the adjustment unit 43 adjusts the duration of at least one of the first period T1 and the second period T2 so that the component value Q1 (DC) and the component value Q2 (DC) are closer to each other (S5). Specifically, the adjustment unit 43 adds or subtracts a predetermined value Δ to or from the duration of the first period T1 or the second period T2. For example, when the component value Q1 (DC) is greater than the component value Q2 (DC), the adjustment unit 43 subtracts the predetermined value Δ from the first period T1 or adds the predetermined value Δ to the second period T2. Conversely, when the component value Q1 (DC) is less than the component value Q2 (DC), the adjustment unit 43 adds the predetermined value Δ to the first period T1 or subtracts the predetermined value Δ from the second period T2. After the adjustment process of step S5, the processes from step S1 to step S4 are repeated again. As understood from the foregoing description, the processes from step S1 to step S5 are repeated so that the component value Q1 (DC) and the component value Q2 (DC) are closer to each other. When the absolute value |Q1 (DC)−Q2 (DC)| is less than the predetermined threshold through the repeated processes from step S1 to step S5 (YES in S4), that is, when the component value Q1 (DC) and the component value Q2 (DC) are closer to each other, the specifying unit 34 specifies the oxygen saturation from the first detection signal PD1 and the second detection signal PD2 generated after the adjustment of the first period T1 and the second period T2 (S6). The report unit 36 instructs the display device 24 to display the oxygen saturation specified by the specifying unit 34 (S7).

As understood from the foregoing description, in the first embodiment, the duration of at least one of the first period T1 and the second period T2 is controlled so that the component value Q1 (DC) of the steady component of the first detection signal PD1 and the component value Q2 (DC) of the steady component of the second detection signal PD2 are closer to each other. Accordingly, compared to a configuration in which the component value Q1 (DC) and the component value Q2 (DC) are not closer to each other, it is possible to generate the first detection signal PD1 and the second detection signal PD2 for compensating a difference in the kinds of tissues in which the first path B1 and the second path B2 are located inside the measurement part M. Further, it is possible to measure biological information with high precision.

As a configuration in which the component value Q1 (DC) of the steady component of the first detection signal PD1 and the component value Q2 (DC) of the steady component of the second detection signal PD2 are closer to each other, a configuration in which a light emission intensity of the light L emitted for the first period T1 and the second period T2 is adjusted can also be considered as well as the configuration of the first embodiment in which the durations of the first period T1 and the second period T2 are adjusted. In a configuration in which the light emission intensity is adjusted, it may be necessary to excessively raise the light emission intensity. However, when coherent light is emitted with an excessively strong intensity, a problem of safety such as erroneous emission to the body of a user may occur. In the configuration of the first embodiment in which the duration of at least one of the first period T1 and the second period T2 is controlled, it is not necessary to emit light with an excessively high light emission intensity. Therefore, even when coherent light is used, the problem of safety is reduced. That is, the first embodiment is particularly effective when coherent light is emitted. In the first embodiment, the light emission intensity of the light L emitted for the first period T1 and the second period T2 is constant. Therefore, it is not necessary to control the light emission intensity.

Second Embodiment

A second embodiment of the invention will be described. In regard to the same elements as those of the first embodiment in operational effects or functions of the following exemplified configurations, the reference numerals used to describe the first embodiment are used and the detailed description thereof will be appropriately omitted.

Figure 7:
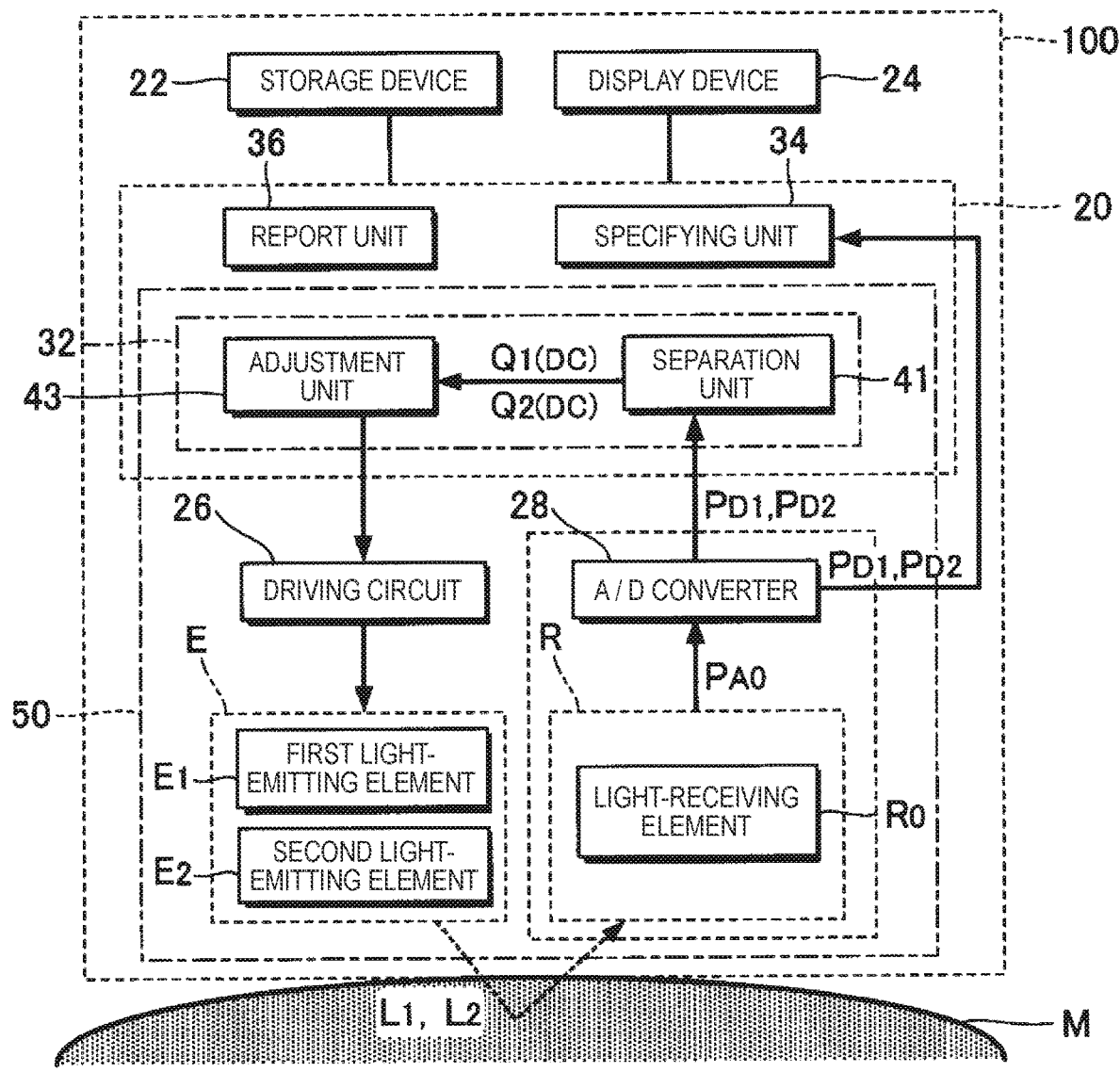
FIG. 7 is a diagram illustrating a functional configuration of a measurement device according to a second embodiment.
Figure 8:
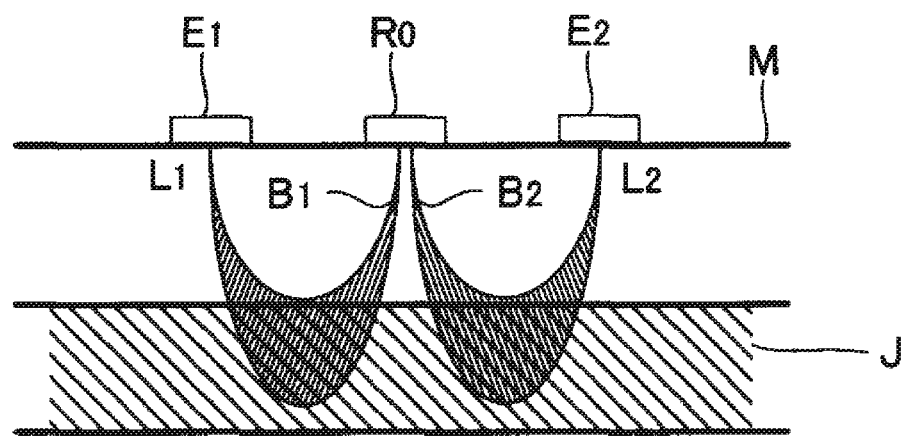
FIG. 8 is a diagram illustrating first and second paths.

FIG. 7 is a diagram illustrating a functional configuration of a measurement device 100 according to the second embodiment. FIG. 8 illustrates a positional relation between a light-emitting unit E and a light-receiving unit R. The light-receiving unit R according to the first embodiment includes the first light-receiving element R1 receiving the light L1 and the second light-receiving element R2 receiving the light L2. The light-receiving unit R according to the second embodiment includes one light-receiving element R0 receiving the light L1 and the light L2, as illustrated in FIGS. 7 and 8. That is, while the separate light-receiving elements R1 and R2 are used to receive the light L1 and the light L2 in the first embodiment, the common light-receiving element R0 is used to receive the light L1 and the light L2 in the second embodiment.

As in the first embodiment, the light-emitting unit E includes the first light-emitting element E1 and the second light-emitting element E2. As exemplified in FIG. 3, the light-emitting unit E emits the light L for each of the first period T1 and the second period T2 alternately repeated at the predetermined cycle C on the time axis. As in the first embodiment, the first light-emitting element E1 emits the light L1 within the first period T1 of the cycle C1 and the second light-emitting element E2 emits the light L2 within the second period T2 of the cycle C2. As in the first embodiment, the light L emitted from the light-emitting unit E (the first light-emitting element E1 and the second light-emitting element E2) is incident on the measurement part M, is repeatedly reflected and scattered inside the measurement part M, is emitted to the side of the detection surface 18, and arrives at the signal generation unit 60 (the light-receiving unit R).

The light-receiving unit R according to the second embodiment includes one light-receiving element R0, as described above. Specifically, as exemplified in FIG. 8, the first light-emitting element E1 and the second the light-emitting element E2 are located opposite and equidistantly with the light-receiving element R0 interposed therebetween. That is, the first light-emitting element E1, the second light-emitting element E2, and the light-receiving element R0 are located on a straight line in an in-plane direction of the detection surface 18. A distance between the first light-emitting element E1 and the light-receiving element R0 (for example, a center-to-center distance) is equal to a distance between the second light-emitting element E2 and the light-receiving element R0.

The light-receiving element R0 receives the light L1 emitted from the first light-emitting element E1 for each first period T1 and passing along the first path B1 inside the measurement part M and the light L2 emitted from the second light-emitting element E2 for each second period T2 and passing along the second path B2 different from the first path B1 inside the measurement part M, and generates a light reception signal PA0 according to the light reception level. That is, the light reception signal PA0 includes both a component according to a light reception level of the light L1 passing along the first path B1 and a component according to a light reception level of the light L2 passing along the second path B2. As exemplified in FIG. 8, the first path B1 and the second path B2 are different from each other since the first light-emitting element E1 and the second light-emitting element E2 are installed at different positions on the detection surface 18 in the measurement part M.

The A/D converter 28 in FIG. 7 generates the same first detection signal PD1 and second detection signal PD2 as those of the first embodiment by performing A/D conversion on the light reception signal PA0 (analog signals) generated by the light-receiving unit R. Specifically, the A/D converter 28 generates a time series of detection values obtained by performing time integration on the light reception signal PA0 within the cycle C1 including the first period T1 as the first detection signal PD1 in FIG. 5 and generates a time series of detection values obtained by performing time integration on the light reception signal PA0 within the cycle C2 including the second period T2 as the second detection signal PD2 in FIG. 5. That is, the A/D converter 28 according to the second embodiment separates the first detection signal PD1 and the second detection signal PD2 from one light reception signal PA to generate the first detection signal PD1 and the second detection signal PD2. As understood from the foregoing description, as in the first embodiment, the light-receiving unit R and the A/D converter 28 function as the signal generation unit 60 that generates the first detection signal PD1 according to the light reception level of the light L1 emitted from the light-emitting unit E for each first period T1 and passing along the first path B1 inside the measurement part M and the second detection signal PD2 according to the light reception level of the light L2 emitted from the light-emitting unit E for each second period T2 and passing along the second path B2 different from the first path B1 inside the measurement part M.

As in the first embodiment, the control unit 32 in FIG. 7 includes the separation unit 41 and the adjustment unit 43 and controls a duration of at least one of the first period T1 and the second period T2 so that the component value Q1 (DC) of the steady component of the first detection signal PD1 and the component value Q2 (DC) of the steady component of the second detection signal PD2 are closer to each other. The oxygen saturation is specified by the specifying unit 34 and the oxygen saturation is reported by the report unit 36, as in the first embodiment.

As understood from the foregoing description, the same advantages as those of the first embodiment can also be obtained in the second embodiment. In the second embodiment, in particular, the common light-receiving element R0 is used to receive the light L1 emitted for the first period T1 and the light L2 emitted for the second period T2. Therefore, the detection device 50 can be further miniaturized than in the first embodiment in which the separate light-receiving elements R1 and R2 are used to receive the light L1 emitted for the first period T1 and the light L2 emitted for the second period T2. In the second embodiment, the positions of the first path B1 and the second path B2 are nearer than in the first embodiment in which the separate light-receiving elements R1 and R2 are used. Therefore, it is easy that the kinds of tissues in which the first path B1 and the second path B2 are located inside the measurement part M are the same. Accordingly, it is possible to generate the first detection signal PD1 and the second detection signal PD2 for compensating a difference in the kinds of tissues with high precision. Further, it is possible to measure biological information with higher precision.

Third Embodiment

Figure 9:
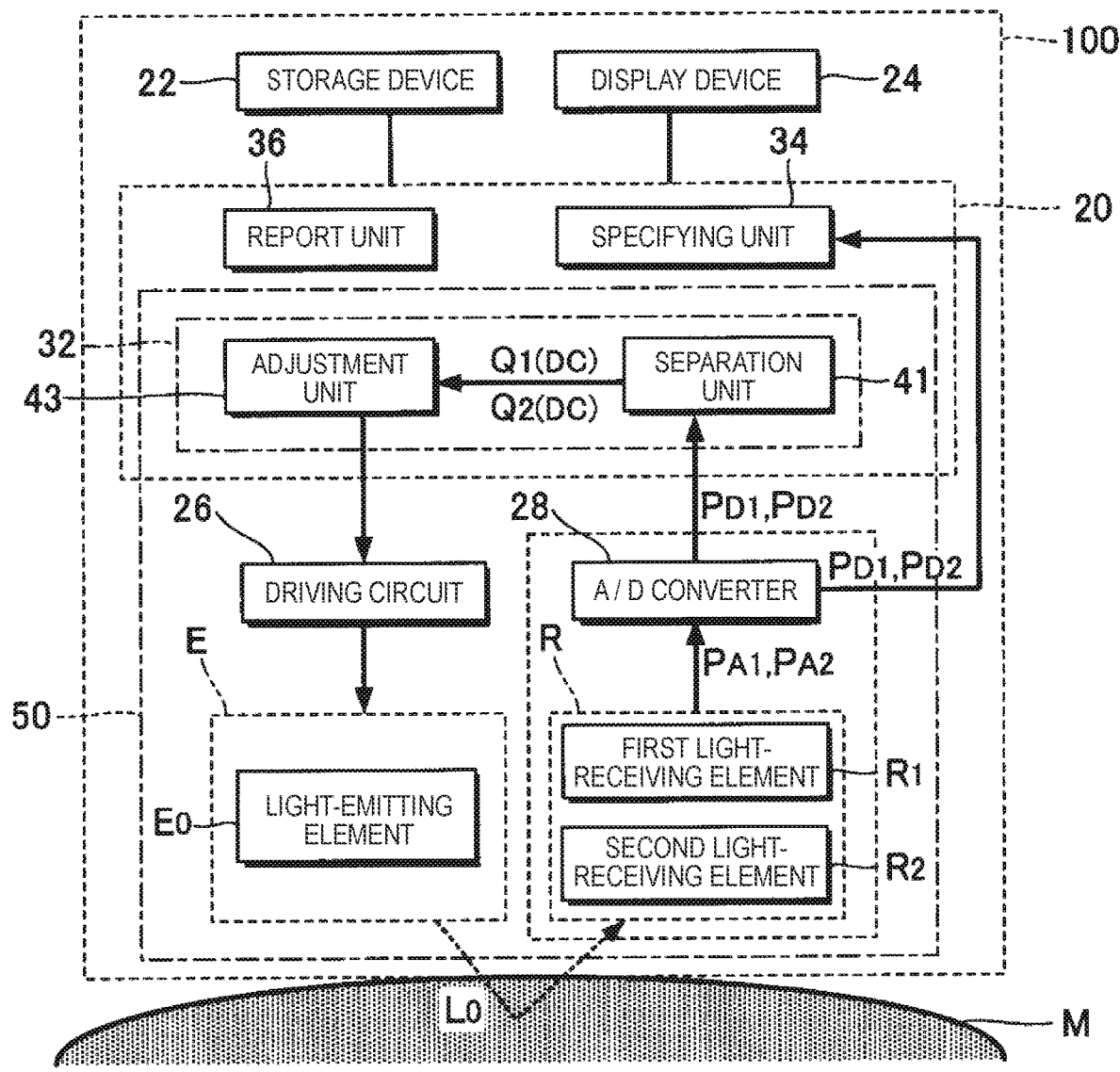
FIG. 9 is a diagram illustrating a functional configuration of a measurement device according to a third embodiment.
Figure 10:
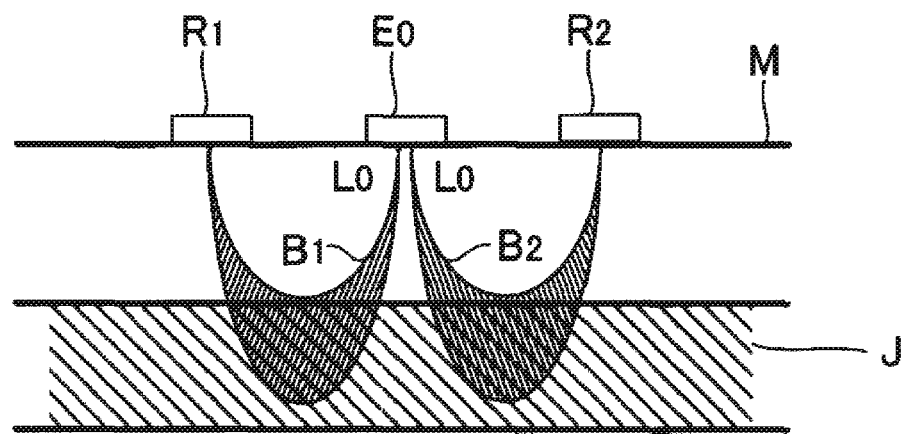
FIG. 10 is a diagram illustrating first and second paths.

FIG. 9 is a diagram illustrating a functional configuration of a measurement device 100 according to a third embodiment. FIG. 10 illustrates a light-receiving unit R and a light-emitting unit E. The light-emitting unit E according to the first embodiment includes a first light-emitting element E1 that emits the light L1 for the first period T1 and a second light-emitting element E2 that emits the light L2 for the second period T2. However, the light-emitting unit E according to the third embodiment includes one light-emitting element E0 that emits light L0, as illustrated in FIGS. 9 and 10.

Figure 11:
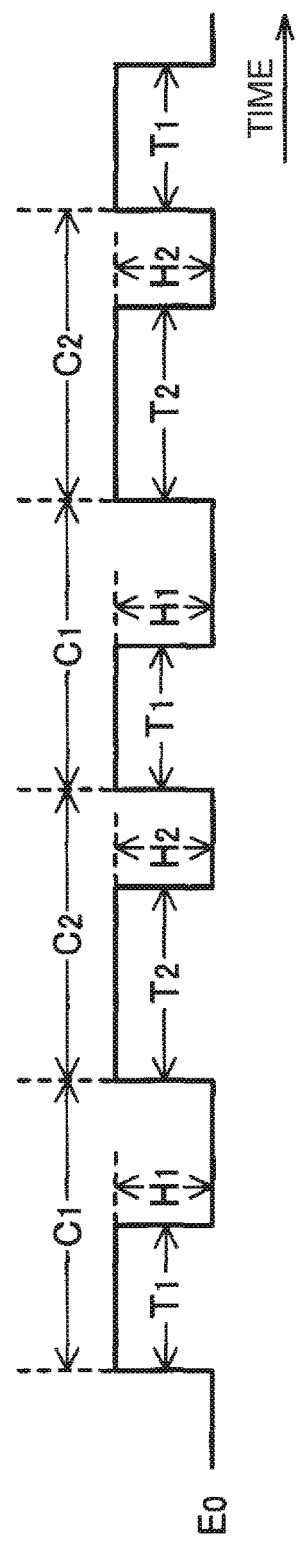
FIG. 11 is a diagram illustrating a light emitting operation by a light-emitting unit.

A wavelength range Δλ of the light L0 is in a range of, for example, 650 nm to 950 nm and includes wavelength of near infrared light (with wavelength λ1=900 nm) and red light (with wavelength λ2=700 nm). FIG. 11 is a diagram illustrating a light emitting operation by the light-emitting unit E. As exemplified in FIG. 11, the light-emitting element E0 emits the light L0 for each of the first period T1 and the second period T2 alternately repeated at the predetermined cycle C on the time axis. The cycle C1 including the first period T1 and the cycle C2 including the second period T2 are alternately repeated on the time axis. Specifically, the light-emitting element E0 emits the light L0 with a light emission intensity H1 for the first period T1 of the cycle C1 and emits the light L0 with a light emission intensity H2 for a duration equivalent to the second period T2 of the cycle C2. The light emission intensity H1 and the light emission intensity H2 may be different. The light-emitting element E0 is turned off for a period other than the first period T1 of the cycle C1 and a period other than the second period T2 of the cycle C2. The driving circuit 26 supplies a driving current to the light-emitting element E0 for the first period T1 and the second period T2 in response to an instruction from the control device 20. Accordingly, the light-emitting element E0 emits the light L0 for each first period T1 and each second period T2.

As in the first embodiment, the light L0 emitted from the light-emitting unit E (the light-emitting element E0) in FIG. 9 is incident on the measurement part M, is repeatedly reflected and scattered inside the measurement part M, is emitted to the side of the detection surface 18, and arrives at the signal generation unit 60 (the light-receiving unit R). The light-receiving unit R according to the third embodiment includes the first light-receiving element R1 and the second light-receiving element R2 and generates the first analog light reception signal PA1 and the second analog light reception signal PA2 according to a light reception level of the light L0 arriving from the measurement part M.

Specifically, as exemplified in FIG. 10, the first light-receiving element R1 and the second light-receiving element R2 are located opposite and equidistantly with the light-emitting element E0 interposed therebetween. That is, the first light-receiving element R1, the second light-receiving element R2, and the light-emitting element E0 are located on a straight line in an in-plane direction of the detection surface 18. A distance between the first light-receiving element R1 and the light-emitting element E0 (for example, a center-to-center distance) is equal to a distance between the second light-receiving element R2 and the light-emitting element E0.

Each of the first light-receiving element R1 and the second light-receiving element R2 includes an optical band-pass filter that selectively transmits light with a specific wavelength. For example, the band-pass filter included in the first light-receiving element R1 transmits near infrared light (with wavelength $\lambda 1 = 900$ nm) and the band-pass filter included in the second light-receiving element R2 transmits red light (with wavelength $\lambda 2 = 700$ nm). That is, the first light-receiving element R1 receives the near infrared light in the light L0 emitted by the light-emitting element E0 and second light-receiving element R2 receives the red light in the light L0 emitted by the light-emitting element E0.

Specifically, the first light-receiving element R1 receives the near infrared light in the light L0 emitted from the light-emitting element E0 for each first period T1 and each second period T2 and passing along the first path B1 inside the measurement part M and generates the first light reception signal PA1 according to the light reception level. Specifically, the second light-receiving element R2 receives the red light in the light L0 emitted from the light-emitting element E0 for each first period T1 and each second period T2 and passing along the second path B2 inside the measurement part M and generates the second light reception signal PA2 according to the light reception level. That is, the first light reception signal PA1 is a signal according to the light reception level of the near infrared light in the light L0 emitted for each first period T1 and each second period T2. The second light reception signal PA2 is a signal according to the light reception level of the red light in the light L0 emitted for each first period T1 and each second period T2. As exemplified in FIG. 10, the first path B1 and the second path B2 are different from each other since the first light-receiving element R1 and the second light-receiving element R2 are installed at different positions on the detection surface 18 in the measurement part M.

The A/D converter 28 in FIG. 9 generates the same first detection signal PD1 and second detection signal PD2 as those of the first embodiment by performing A/D conversion on the light reception signal PA (analog signal) generated by the light-receiving unit R. Specifically, the A/D converter 28 generates a time series of detection values obtained by performing time integration on the first light reception signal PA1 within the cycle C1 including the first period T1 as the first detection signal PD1 in FIG. 5 and generates a time series of detection values obtained by performing time integration on the second light reception signal PA2 within the cycle C2 including the second period T2 as the second detection signal PD2 in FIG. 5.

As understood from the foregoing description, as in the first embodiment, the light-receiving unit R and the A/D converter 28 function as the signal generation unit 60 that generates the first detection signal PD1 according to the light reception level of the light L0 emitted from the light-emitting unit E for each first period T1 and passing along the first path B1 inside the measurement part M and the second detection signal PD2 according to the light reception level of the light L0 emitted from the light-emitting unit E for each second period T2 and passing along the second path B2 different from the first path B1 inside the measurement part M.

As in the first embodiment, the control unit 32 in FIG. 9 includes the separation unit 41 and the adjustment unit 43 and controls a duration of at least one of the first period T1 and the second period T2 so that the component value Q1 (DC) of the steady component of the first detection signal PD1 and the component value Q2 (DC) of the steady component of the second detection signal PD2 are closer to each other. The oxygen saturation is specified by the specifying unit 34 and the oxygen saturation is reported by the report unit 36, as in the first embodiment.

As understood from the foregoing description, the same advantages as those of the first embodiment can also be obtained in the third embodiment. In the third embodiment, in particular, the common light-emitting element E0 is used to emit the light L0 for the first period T1 and the second period T2. Therefore, the detection device 50 can be further miniaturized than in the first embodiment in which the separate light-emitting elements E1 and E2 are used to emit the light L for the first period T1 and the second period T2. In the third embodiment, the positions of the first path B1 and the second path B2 are nearer than in the first embodiment in which the separate light-receiving elements R1 and R2 are used. Therefore, it is easy that the kinds of tissues in which the first path B1 and the second path B2 are located inside the measurement part M. Accordingly, it is possible to generate the first detection signal PD1 and the second detection signal PD2 for compensating a difference in the kinds of tissues with high precision. Further, it is possible to measure biological information with higher precision.

Modification Examples

The modes exemplified above can be variously modified. Specific modification forms will be exemplified below. Any two or more forms selected from the following examples can also be combined appropriately.

(1) In the first and second embodiments, the wavelengths $\lambda$ of the first light-emitting element E1 and the second light-emitting element E2 are different. However, any specific numerical values or difference between the wavelengths $\lambda$ of the first light-emitting element E1 and the second light-emitting element E2 can be used. For example, when a blood pressure is specified as biological information, the wavelengths $\lambda$ of the first light-emitting element E1 and the second light-emitting element E2 can also be set to be the same.

(2) In the above-described embodiments, the average value $((K_{max1}+K_{min1})/2)$ of the maximum value $K_{max1}$ and the minimum value $K_{min1}$ of the amplitude of the first detection signal PD1 is calculated as the component value Q1 (DC) of the steady component, but the method of calculating the component value Q1 (DC) is not limited to the above example. For example, the minimum value $K_{min1}$ of the amplitude of the first detection signal PD1 can also be calculated as the component value Q1 (DC) of the steady component. The component value Q1 (DC) can also be calculated by applying the first detection signal PD1 to a low-pass filter. This is true for the second detection signal PD2.

(3) In the above-described embodiments, the durations (duty ratio) of the first period T1 and the second period T2 is adjusted while the duration of each cycle C is constant. As the method of adjusting the durations of the first period T1 and the second period T2, a method of changing the duration of the cycle C1 according to the duration of the first period T1, changing the duration of the cycle C2 according to the duration of the second period T2 can also be used. Here, in the above-described configuration in which the durations of the first period T1 and the second period T2 are controlled while maintaining the duration of each cycle C to be constant, the duration of each cycle C is constant. Therefore, time resolutions of the first detection signal PD1 and the second detection signal PD2 are normally constant.

(4) In the above-described embodiments, the adjustment unit 43 adjusts the durations of the first period T1 and the second period T2 so that the durations of the first period T1 and the second period T2 are closer to each other by adding or subtracting the predetermined value $\Delta$ to or from the duration of the first period T1 or the second period T2.

However, the method of adjusting the durations of the first period T1 and the second period T2 is not limited to the above example. For example, the duration of the first period T1 or the second period T2 can also be adjusted by a variable adjustment amount according to a difference between the component value Q1 (DC) and the component value Q2 (DC). For example, a configuration in which the adjustment amount is larger by the difference is suitable. In the foregoing configuration, it is possible to quickly approach the component value Q1 (DC) and the component value Q2 (DC) to each other.

(5) The light-emitting unit E according to the first and second embodiments includes the first light-emitting element E1 and the second light-emitting element E2. The light-emitting unit E according to the third embodiment includes one light-emitting element E0. That is, irrespective of the number of light-emitting elements, the light-emitting unit E is inclusively expressed as a component that emits the light L to the measurement part M for each of the first period T1 and the second period T2 repeated on the time axis. Here, in the configurations of the first and second embodiments in which the first light-emitting element E1 and the second light-emitting element E2 are included, a configuration in which the light L with a different wavelength range from the first period T1 and the second period T2 is emitted can be realized more easily than in the configuration of the third embodiment in which only one light-emitting element E0 is included. Accordingly, the configurations of the first and second embodiments are particularly effective when coherent light with a narrow wavelength range is emitted.

(6) The light-receiving unit R according to the first and third embodiments includes the first light-receiving element R1 and the second light-receiving element R2. The light-receiving unit R according to the second embodiment includes one light-receiving element R0. That is, irrespective of the number of light-receiving elements, the light-receiving unit R is inclusively expressed as a component that receives the light L emitted from the light-receiving unit R for each first period T1 and passing along the first path B1 inside the measurement part M and the light L emitted from the light-receiving unit R for each second period T2 and passing along the second path B2 inside the measurement part M and generates the light reception signals PA according to the light reception levels. Here, in the configurations of the first and third embodiments in which the first light-receiving element R1 and the second light-receiving element R2 are included, compared to a configuration of the second embodiment in which only one light-receiving element R0 is included, it is possible to individually optimize light reception characteristics (light reception sensitivity in a specific bandwidth) of the first light-receiving element R1 and the second light-receiving element R2. For example, in the first embodiment, there is the advantage in which a detection signal with a high SN ratio can be acquired by using the first light-receiving element R1 with high light reception sensitivity with respect to the light L1 with the wavelength X1 and the second light-receiving element R2 with high light reception sensitivity with respect to the light L2 with the wavelength $\lambda2$ (further, it is possible to measure biological information with higher precision).

Figure 12:
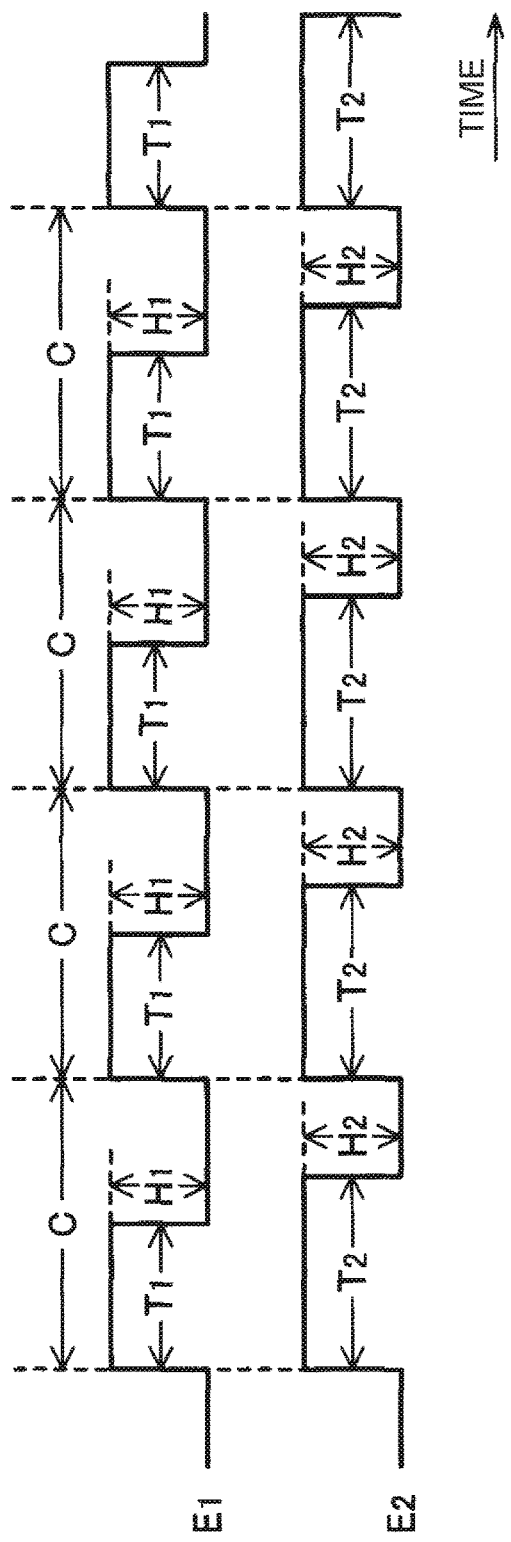
FIG. 12 is a diagram illustrating a light emitting operation by a light-emitting unit according to modification examples.

(7) In the above-described embodiments, the cycle C1 including the first period T1 and the cycle C2 including the second period T2 are alternately repeated on the time axis. In the first embodiment, however, the invention is not limited to the above example. For example, in the first embodiment, the pair of first light-emitting element E1 and first light-receiving element R1 and the pair of second light-emitting element E2 and second light-receiving element R2 are independent. Therefore, as exemplified in FIG. 12, the first period T1 and the second period T2 can be provided in each cycle C. Specifically, the first light-emitting element E1 emits the light L1 within the first period T1 of the cycle C and is turned off for a period other than the first period T1 of the cycle C. The second light-emitting element E2 emits the light L2 for a duration equivalent to the second period T2 of the cycle C and is turned off for a period other than the second period T2 of the cycle C. The light L1 and the light L2 are emitted at each cycle C. In the foregoing configuration, it is not necessary to alternately repeat the cycle C1 and the cycle C2 on the time axis. Therefore, time resolutions of the first detection signal PD1 and the second detection signal PD2 are raised. As understood from the foregoing description, the light-emitting unit E is inclusively expressed as a component that emits the light L to the measurement part M for each of the first period T1 and the second period T2 repeated on the time axis.

(8) In the above-described embodiments, the light L emitted by the light-emitting unit E is coherent light, but the light L emitted by the light-emitting unit E can also be incoherent light. As described above, however, in the configurations of the above-described embodiments in which the duration of at least one of the first period T1 and the second period T2 is controlled, it is not necessary to emit the light with excessively high light emission intensity. Therefore, the problem of safety particularly cautious when coherent light is used is reduced. That is, the configurations of the above-described embodiments in which the duration of at least one of the first period T1 and the second period T2 is controlled are particularly effective when coherent light is emitted.

(9) In the third embodiment, the first detection signal PD1 according to the light reception level of the near infrared light is generated when the component with the wavelength $\lambda1$ in the light L0 emitted by the light-emitting unit E is selected by the optical band-pass filter. However, by separating the component according to the light reception level of the near infrared light in the light reception signal generated by the first light-receiving element R1 through signal processing (filter processing), it is possible to also generate the first detection signal PD1. This is true for the second detection signal PD2.

(10) In the above-described embodiments, the oxygen saturation is specified with reference to the table in which each numerical value of the oxygen saturation matches each numerical value of the variation ratio $\Phi$ calculated by Formula (2), but the oxygen saturation can also be specified through calculation.

(11) In the above-described embodiments, the oxygen saturation is measured, but the kind of biological information is not limited to the above example. For example, a configuration in which a pulse, a blood flow rate, or blood pressure is measured as biological information and a configuration in which various blood component concentrations such as a glucose concentration in blood, a hemoglobin concentration, an oxygen concentration in blood, and a neutral fat concentration are measured as biological information can also be adopted.

(12) In the above-described embodiments, the measurement device 100 generates and displays biological information, but a separate device from the measurement device 100 can also generate and display biological information. For example, a terminal device (for example, a mobile phone or a smartphone) capable of communicating with the measurement device 100 can also generate and display biological information. Specifically, the measurement device 100 generates the first detection signal PD1 and the second detection signal PD2 and transmits the first detection signal PD1 and the second detection signal PD2 to the terminal device. The terminal device generates biological information from the first detection signal PD1 and the second detection signal PD2 received from the measurement device 100 and causes the display device of the terminal device to display the biological information. According to this modification example, one or both of the storage device 22 and the display device 24 can also be configured to be included in the terminal device. One or both of the specifying unit 34 and the report unit 36 may be configured to be included in the terminal device (for example, a configuration in which an application executed by the terminal device is realized). As understood from the foregoing description, the measurement device 100 can also be realized in a plurality of devices configured to be separated from each other.

(13) In the above-described embodiments, the measurement device 100 configured to include the belt 14 and the casing 12 is exemplified, but any specific form of the measurement device 100 can be used. For example, any measurement device 100 such as a patch type of device attached to the body of a test subject, an earring type of device mounted on an auricle of a test subject, a finger-mounted type of device mountable at a fingertip (for example, a nail-mounted type), and a head-mounted type of device mountable on the head of a test subject can be adopted. However, for example, in a state in which the finger-mounted type of measurement device 100 is mounted, a possibility of a daily life being obstructed is assumed. Therefore, from the viewpoint that blood pressure is normally measured without obstructing a daily life, the measurement device 100 mountable on a wrist of a test subject by the belt 14, as described above, is particularly suitable. The measurement device 100 mounted (for example, externally mounted) on any of various electronic apparatuses such as a wristwatch can also be realized.

(14) In the invention, a method of operating the detection device 50 (a detection method) can also be specified. Specifically, a detection method 50 in a preferred mode of the invention is a detection method of generating the first detection signal PD1 and the second detection signal PD2 used to specify biological information and causes a computer to perform: emitting the light L to the measurement part M for each of the first period T1 and the second period T2 repeated on the time axis; generating the first detection signal PD1 according to the light reception level of the light L1 emitted for each first period T1 and passing along the first path B1 inside the measurement part M and the second detection signal PD2 according to the light reception level of the light L1 emitted for each second period T2 and passing along the second path B2 different from the first path B1 inside the measurement part M; and controlling the duration of at least one of the first period T1 and the second period T2 so that the component value Q1 (DC) of the steady component of the first detection signal PD1 and the component value Q2 (DC) of the steady component of the second detection signal PD2 are closer to each other.

The entire disclosure of Japanese Patent Application No. 2016-165584 is hereby incorporated herein by reference.

What is claimed is:

1. A detection device for generating first and second detection signals used to specify biological information, the detection device comprising:

at least one light emitting diode (LED) configured to emit light to a measurement part for each of first and second periods repeated on a time axis;

at least one optical sensor configured to detect the light emitted from the at least one LED; and a processor programmed to:

generate the first detection signal according to a light reception level of the detected light for each first period and passing along a first path inside the measurement part, generate the second detection signal according to a light reception level of the detected light for each second period and passing along a second path different from the first path inside the measurement part; and control a duration of at least one of the first and second periods so that an absolute difference of component values of steady components included in the first and second detection signals is less than or equal to a predetermined threshold.

2. The detection device according to claim 1, wherein the first and second periods are alternately repeated at a predetermined cycle.

3. The detection device according to claim 1, wherein the light is coherent light.

4. The detection device according to claim 1, wherein the at least one LED includes:

a first light-emitting element that emits the light passing along the first path for the first period, and a second light-emitting element that emits the light passing along the second path for the second period.

5. The detection device according to claim 1, wherein the at least one optical sensor includes a first light-receiving element that receives the light passing along the first path and a second light-receiving element that receives the light passing along the second path, the processor generates the first detection signal according to a light reception level of the light received by the first light-receiving element, and the processor generates the second detection signal according to a light reception level of the light received by the second light-receiving element.

6. The detection device according to claim 1, wherein a light emission intensity of the light emitted for each first period by the at least one LED and passing along the first path is constant and a light emission intensity of the light emitted for each second period by the at least one LED and passing along the second path is constant.

7. A detection method for generating first and second detection signals used to specify biological information, the detection method comprising:

emitting light to a measurement part for each of first and second periods repeated on a time axis;

generating the first detection signal according to a light reception level of the light emitted for each first period and passing along a first path inside the measurement part;

generating the second detection signal according to a light reception level of the light emitted for each second period and passing along a second path different from the first path inside the measurement part; and controlling a duration of at least one of the first and second periods so that an absolute difference of component values of steady components included in the first and second detection signals is less than or equal to a predetermined threshold.

* * * * *